(12) United States Patent
Boettcher

(10) Patent No.: US 6,405,582 B1
(45) Date of Patent: Jun. 18, 2002

(54) BIOSENSOR AND DEPOSIT SENSOR FOR MONITORING BIOFILM AND OTHER DEPOSITS

(75) Inventor: Helmut Boettcher, Jülich (DE)

(73) Assignee: Hercules Incorporated, Wilmington, DE (US)

(*) Notice: Subject to any disclaimer, the term of this patent is extended or adjusted under 35 U.S.C. 154(b) by 0 days.

(21) Appl. No.: 09/657,341

(22) Filed: Sep. 7, 2000

Related U.S. Application Data

(60) Provisional application No. 60/211,682, filed on Jun. 15, 2000.

(51) Int. Cl.[7] ............................................. G01N 15/04
(52) U.S. Cl. ..................................... 73/61.72; 73/61.62
(58) Field of Search ............................ 73/61.62, 61.63, 73/61.71, 61.72, 86; 210/698, 699; 356/632; 165/11.1

(56) References Cited

U.S. PATENT DOCUMENTS

| | | | |
|---|---|---|---|
| 2,090,077 A | | 8/1937 | Thorne ...................... 73/61.72 |
| 2,397,038 A | * | 3/1946 | Obenshain et al. ......... 73/61.71 |
| 3,253,219 A | * | 5/1966 | Littler ........................... 73/86 |
| 3,943,754 A | * | 3/1976 | Orr, Jr. ....................... 73/61.63 |
| 3,992,249 A | * | 11/1976 | Farley .......................... 162/72 |
| 4,092,244 A | | 5/1978 | Suen et al. ................... 210/699 |
| 4,383,438 A | * | 5/1983 | Eaton ......................... 73/61.62 |
| 5,049,492 A | | 9/1991 | Sauer et al. .................... 435/30 |
| 5,068,196 A | * | 11/1991 | Hays et al. ................. 73/61.62 |
| 5,123,203 A | | 6/1992 | Hiromoto ....................... 47/1.1 |
| 5,155,555 A | | 10/1992 | Wetegrove et al. .......... 356/632 |
| 5,264,917 A | | 11/1993 | Wetegrove et al. .......... 356/632 |
| 5,492,005 A | * | 2/1996 | Homan et al. .............. 73/61.62 |
| 5,536,363 A | | 7/1996 | Nguyen .......................... 162/5 |
| 5,589,106 A | * | 12/1996 | Shim et al. ................... 252/387 |
| 5,798,023 A | * | 8/1998 | Pruszynski et al. ........ 162/181.1 |
| 5,814,221 A | * | 9/1998 | Cervantes ..................... 210/542 |
| 6,017,459 A | | 1/2000 | Zeiher et al. ................ 210/650 |
| 6,053,032 A | | 4/2000 | Kraus et al. ................. 73/61.62 |
| 6,139,830 A | * | 10/2000 | Donlan et al. .............. 424/78.09 |
| 6,250,140 B1 | * | 6/2001 | Kouznetsov et al. ........... 73/86 |
| 6,258,226 B1 | * | 7/2001 | Conner ......................... 204/279 |

FOREIGN PATENT DOCUMENTS

| | | | | |
|---|---|---|---|---|
| EP | 0 433 053 | | 6/1991 | |
| GB | 1 462 746 | | 1/1977 | |
| JP | 56104235 A | * | 8/1981 | ..................... 73/86 |
| JP | 01086038 A | * | 9/1987 | ................. 73/61.72 |
| JP | 62250332 A | * | 10/1987 | ................. 73/61.72 |
| WO | WO 91 00002 | | 1/1991 | |
| WO | WO-9117423 | * | 11/1991 | ..................... 73/86 |

OTHER PUBLICATIONS

Schlegel H. G. "Allegemeine Mikrobiologie" 1992, Georg Thieme Verlag Stuttgart, New York p. 225.

* cited by examiner

*Primary Examiner*—Hezron Williams
*Assistant Examiner*—Michael Cygan
(74) *Attorney, Agent, or Firm*—Joanne Rossi

(57) ABSTRACT

A method and apparatus for determining the deposition of organic and inorganic contaminants, such as biofilm, on a coupon is disclosed. The method and apparatus include a coupon suspended from a weight sensor within a reservoir tank. The reservoir tank includes fluid inlet means for receiving a fluid sample which flows over the surface of the coupon for a predetermined period of time to allow contaminants present in the fluid sample to deposit on the coupon surface. At regular intervals, the reservoir tank is drained and the coupon is allowed to dry and is weighed. The weight of the contaminants which have deposited on the surface of the coupon is determined by comparing the weight of the coupon to its previous weight. In this manner, a computer system attached to the weight sensor can analyze a series of weights and present the results in a time-deposit graph. The present invention can be fully automated to allow for effective and optimal biocidal whitewater treatments to occur in pulp and papermaking processes, and is well suited for use in screening biocidal agents effective in preventing the deposition of contaminants on equipment surfaces.

17 Claims, 1 Drawing Sheet

BIOSENSOR AND DEPOSIT SENSOR FOR MONITORING BIOFILM AND OTHER DEPOSITS

This application claims the benefit of U.S. Provisional Application No. 60/211,682, filed on Jun. 15, 2000.

FIELD OF THE INVENTION

The present invention relates to. a method and apparatus for measuring the growth of biological material and the deposition of organic and inorganic contaminants on coupons, and for screening agents useful for regulating the growth of biological material and the deposition of organic and inorganic contaminants. More particularly, the present invention is directed to a method and apparatus for measuring the growth of biological material and the deposition of organic and inorganic contaminants on coupons.

BACKGROUND OF RELATED TECHNOLOGY

Many industrial processes, such as pulp and paper making, utilize water and/or other liquid material in processing steps. Such process liquid typically provides an excellent supply of carbon and nutrients which promote bacterial growth. In paper mills, for instance, bacterial films ("biofilms") undesirably and readily forms on the steel surfaces of process equipment used during manufacture. Such biofilms typically are accompanied by protective exopolysaccharides ("slime") and occur at the interface of these equipment surfaces and process water streams. Additionally, inorganic contaminants, such as calcium carbonate ("scale") and organic contaminants often deposit on such surfaces. These organic contaminants are typically known as pitch (e.g., resins from wood) and stickies (e.g., glues, adhesives, tape, and wax particles).

The growth of biofilm and the deposition of these inorganic and organic contaminants can be detrimental to the efficiency of such equipment causing both reduced product quality, reduced operating efficiency, and general operational difficulties in the systems. Deposition of organic contaminants on consistency regulators and other instrument probes can render these components useless, and deposits on screens can reduce throughput and upset operation of the system. This deposition can occur not only on metal surfaces in the system, but also on plastic and synthetic surfaces such as machine wires, felts, foils, Uhle boxes and headbox components. The difficulties posed by these deposits include direct interference with the efficiency of the contaminated surface, resulting in reduced production, as well as holes, dirt, and other sheet defects that reduce the quality and usefulness of the paper for operations that follow like coating, converting or printing.

Consequently, methods of preventing and removing the build-up of such deposits on pulp and paper mill equipment surfaces are of great industrial importance. While paper machines can be shut down for cleaning, this is undesirable as it necessarily results in a loss of productivity of the machine. Additionally, the product produced prior to such cleaning is often of poor quality due to contamination from deposits which break off and become incorporated into product sheets. Likewise, removing such deposits also necessarily results in the formation of poor quality product which is manufactured prior to such deposition removal. Preventing deposition of such contaminants is thus greatly preferred as it allows for consistently high quality product to be produced in an efficient manner.

Additionally, the deposition of slime and other contaminants on metal surfaces promotes both corrosion of such surfaces and fouling or plugging of pulp and paper mill systems. Typically, the deposits become entrained in the paper produced and cause breakouts on the paper machines with consequent work stoppages and the loss of production time. These deposits also causes unsightly blemishes in the final product, resulting in rejects and wasted output.

These contamination problems have resulted in the extensive utilization of contamination control agents, such as biocides, in water used in pulp and paper mill systems. Agents which have enjoyed widespread use in such applications include chlorine, organo-mercurials, chlorinated phenols, organo-bromines, and various organosulfur compounds, all of which are generally useful as biocides but each of which is attended by a variety of impediments. Particularly, the use of compositions comprising polyvinyl alcohol and gelatin, such as those described in U.S. Pat. No. 5,536,363 to Nguyen, have been found to be well suited for regulating the deposition of organic contaminants in pulp and papermaking systems. Further, conditions such as temperature, pH, and the presence of organic and inorganic materials vary greatly among and within manufacturing processes, resulting in a need for agents which serve to destroy and regulate the growth of such materials that form on process equipment functioning under these various conditions.

It is known to monitor the presence of biofilm and other contaminant materials in process water streams, such as through the methods and apparatuses described in U.S. Pat. No. 2,090,077 to Thorne, U.S. Pat. No. 5,049,492 to Sauer et al., U.S. Pat. No. 5,155,555 and 5,264,917 both to Wetegrove et al., U.S. Pat. No. 6,017,459 to Zeiher et al., and U.S. Pat. No. 6,053,032 to Kraus et al. which allow for the sampling of water during manufacturing processes.

As illustrated by these references, known methods and apparatuses for determining the presence of contaminants in process water streams include contacting a substrate, known in the art as a coupon, with a process water stream for a period of time, removing the substrate from the stream, and then subjecting the coupon to analysis. Such analysis typically involves staining and microscopy, visual inspection, or light transmission. Each of these methods and apparatuses, however, has drawbacks such as requiring that the coupon be removed from the fluent sample and attended to by a person for analysis. Further, the qualitative nature of certain methods, such as staining and microscopy, make it difficult to reproduce results obtained thereby when such methods are part of an experimental design.

Accordingly, there exists a need for a method and apparatus which allows for the continuous and automatic quantitative measuring of the deposition of biofilm and other contaminants on a coupon in process water streams and which allow for the investigation of agents useful for regulating contaminant deposition.

SUMMARY OF THE INVENTION

In a method aspect of the present invention, the present invention provides a method for measuring the deposition of organic and inorganic contaminants on a coupon. The method includes the steps of: (i) supporting a coupon in a fluid sample; (ii) separating the coupon from the fluid sample; and (iii) weighing the coupon. The weight of the coupon increases where contaminants present in the fluid sample deposit on the coupon.

The present invention may also include the step of permitting the coupon to dry for a predetermined period of time prior to weighing and may include the step of measuring the weight of the coupon prior to supporting the coupon in the fluid sample. Successive weight measurements may be taken at predetermined intervals and the difference between these successive weight measurements may be recorded. Further, the coupon may be separated from the fluid sample, which may be provided as a current across the coupon, by draining the fluid sample-from the coupon. Contaminant control agents, such as biocides, may also be added manually or automatically to the source of the fluid sample to control the presence of contaminants, such as biofilm, in the source.

In another aspect of the present invention is provided an apparatus for measuring the deposition of contaminants, such as biofilms, on a coupon. The apparatus includes a reservoir tank defining a reservoir cavity for receiving a coupon, a fluid inlet means in fluid communication with the reservoir cavity, a fluid outlet means in fluid communication with the reservoir cavity, a coupon suspension member adapted for supporting a coupon within the reservoir cavity, and a weight sensor coupled to the coupon suspension member. The fluid sample contacts a coupon supported by the coupon suspension member.

The apparatus may further include a substantially elongate planar coupon supported by the coupon suspension means and may include a computer system associated with the weight sensor means which is capable of computing data received from the weight sensor so as to determine the weight of the coupon and any contaminant deposition thereon. The reservoir tank may include a valve for draining the fluid sample from the reservoir cavity.

Further, the apparatus may include a first fluid circuit line in fluid communication with the reservoir tank, where the first fluid circuit line permits the fluid sample to enter the reservoir tank. Additionally, the apparatus may include a second fluid circuit line in fluid communication with the reservoir tank, where the second fluid circuit line permits the fluid sample to exit the reservoir tank. A pump may also be included for drawing the fluid sample from a fluid source to the reservoir tank.

DETAILED DESCRIPTION OF THE INVENTION

Figure 1:
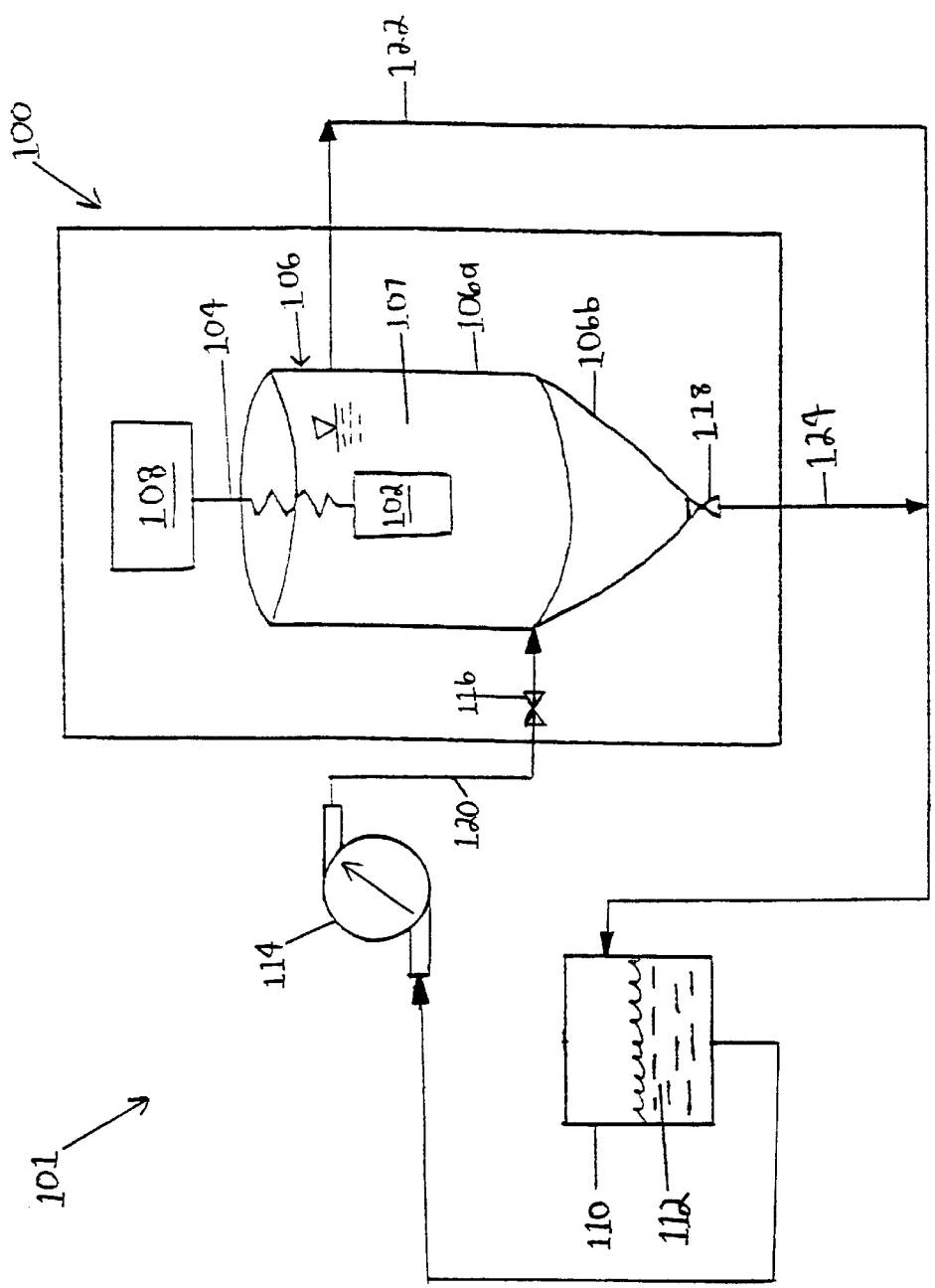
FIG. 1 is a diagrammatic representation of a system and method of the present invention.

The present invention is well suited for monitoring the growth of biofilm and the deposition of organic and inorganic contaminants, such growths and deposits hereinafter referred to as contaminants, in a process water stream as well as for screening contaminant control agents, such as biocides, which serve to regulate the deposition of contaminants on equipment surfaces. Such contaminants include, for example, bacteria, fungi, yeast, algae, diatoms, protozoa, macroalgae, and the like, which flourish in paper process water due to the presence of organic and inorganic materials present therein.

Referring to FIG. 1, a fluid analysis system 100 of the present invention is shown as employed in a closed circuit system 101. A coupon 102 is suspended from a weight sensor 108 by a coupon suspension member 104, such as a spring or fixed arm. Coupon 102 is of such composition, size, and shape as to model the surfaces of equipment used in industrial processes. For example, in order to measure the deposition of contaminants on equipment surfaces such as those found in pulp and papermaking processes, a stainless steel coupon is used as the surface of such equipment is typically composed of steel. Coupon suspension member 104 transfers the weight force of coupon 102 to weight sensor 108 which transduces a signal corresponding to the weight of coupon 102 to a computing or display device (not shown) associated with weight sensor 108. Prior to exposure to the fluid sample, coupon 102 is weighed to provide a baseline measurement. The computing device allows for subsequent weight measurements obtained to be analyzed and presented.

System 100 includes a reservoir tank 106 which defines a reservoir cavity 107 for receiving coupon 102 and processwater 112 therethrough. Reservoir tank 106 includes a cylindrical wall 106a and conical wall 106b. Conical wall 106b is adapted to receive drainage valve 118, which is a directional flow valve. Weight sensor 108 may be any sensor device capable of measuring the weight force of coupon 102 and may include a means for displaying data received thereby.

Coupon 102 is suspended within reservoir tank 106 which is adapted to receive processwater 112. Processwater 112 is supplied by a source 110, which may be a sample container or which may be common to a processwater stream. Processwater 112 is drawn by a pump 114 to flow through a first fluid circuit line 120 which is in fluid communication with reservoir tank 106. Influent control valve 116 adjusts the flow of processwater 112. When drainage valve 118 is closed, this influent processwater stream causes processwater 112 to fill reservoir tank 106 and contact coupon 102 suspended therein.

The fluid level within reservoir tank 106 is controlled so as. to cause fluid to contact the entire surface of coupon 102 without spilling out over the open top of reservoir tank 106. This may be accomplished by positioning a second fluid circuit line 122 in fluid communication with reservoir tank 106, as shown in FIG. 1. Second fluid circuit line 122 serves as a runoff for the effluent processwater stream to prevent reservoir tank 106 from overflowing and is desirably located at a level where coupon 102 is defined submerged in processwater 112 during system operation. Processwater 112 flows through second fluid circuit line 122 and returns to source 110. As processwater 112 flows over the surface of coupon 102, contaminants from the processwater 112 will deposit on coupon 102.

At a predetermined time, drainage valve 118 is opened, preventing processwater 112 from entering the upper portion of reservoir tank 106, defined by cylindrical wall 106a. When drainage valve 118. is opened, processwater 112 within reservoir tank 106 drains out a third fluid circuit line 124. Third fluid circuit line 124 may drain into second fluid circuit line 122, as shown in FIG. 1, thereby returning processwater 112 to source 110, or may open to an alternate collection means. Reservoir tank 106 may be either drained completely or sufficiently to fully expose coupon 102.

Coupon 102 is subsequently allowed to dry for a predetermined period of time, allowing excess processwater present on the surface of coupon 102 to evaporate. As the contaminants which deposit on coupon 102 include water,. the predetermined time for allowing coupon 102 to dry should be long enough to allow all residual processwater on the surface of coupon 102 to evaporate but not so long as to allow any water which is part of the natural biological deposits on coupon 102 to evaporate. As such, an accurate representation of biofilm formation and contaminant deposition may be realized.

At the predetermined time, weight sensor 108 measures the weight of coupon 102 and the resulting data is inputted to a computing device (not shown) associated with weight sensor 108. From the first weight measurement that is taken is subtracted the baseline weight of coupon 102. The resultant weight represents the weight of the contaminants which have deposited on the coupon 102. Subsequently, drainage valve 118 is closed and pump 114 again forces processwater 112 through first fluid circuit line 120 and into reservoir tank 106. The processwater 112 is again permitted to flow over the surface of coupon 102 for a period of time after which reservoir tank 106 is drained, and coupon 102 is allowed to dry before weighing in the manner indicated above. Accordingly, a series of weight measurements are taken with the marginal difference between successive weight measurements of coupon 102 representing the weight of contaminants which have deposited on coupon 102 in the intervening period of time.

A computing means associated with weight sensor 108 is capable of analyzing this information to provide a detailed output of the results. In this manner, the effectiveness of biocidal treatments to processwater 112 at source 110 can be determined efficiently. The present invention can be under the control of a computer system, fully automating the process of operating drainage valve 118, pump 114, and weight sensor 108. As such, the present invention may be used in industrial processes such that biocidal agents are automatically added to processwater 112 at source 110 when unacceptable contaminant deposition is detected. Further, measurement of the continuous build up of deposits on coupon 102 allows for the determination of the effectiveness of various biocidal treatments and permits for the optimization of such treatments.

As will be apparent to one of skill in the art, the present invention is well suited for analysis of fluid samples present in industrial processes, such as pulp and papermaking, as well as in experimental assay techniques. For instance, where the natural flow of whitewater 112 provides sufficient force to move whitewater 112 through first fluid circuit line 120 and into reservoir tank 106, pump 114 is not needed. Accordingly, while the present invention has been shown and described herein, it is to be understood that the foregoing description and accompanying drawings are offered by way of illustration only and not as a limitation. The scope of the invention is defined by the following claims.

What is claimed is:

1. A method for measuring the deposition of contaminants on a coupon, comprising the steps of:
   (i) supporting a coupon in a fluid sample contained in a reservoir;
   (ii) removing said fluid from said coupon; and
   (iii) weighing said coupon in said reservoir;
wherein the weight of said coupon increases where contaminants present in said fluid sample deposit on said coupon.

2. The method of claim 1, further comprising the step of permitting said coupon to dry for a predetermined period of time prior to said weighing step.

3. The method of claim 1, wherein said removing step further comprises draining said fluid sample from said reservoir.

4. The method of claim 1, wherein said fluid sample is provided as a current across said coupon.

5. The method of claim 1, further comprising the step of measuring the weight of said coupon prior to said supporting step.

6. The method of claim 1, further comprising the step of taking successive weight measurements of said coupon at predetermined time intervals.

7. The method of claim 6, further comprising the step of recording the difference between said successive weight measurements.

8. The method of claim 1, further comprising the step of causing biocidal agents to be added to a source of said fluid sample to control the deposition of said contaminants.

9. The method of claim 8, wherein said biocidal agents are added automatically to said fluid sample in response to measurements taken during said weighing step.

10. An apparatus for measuring the deposition of contaminants on a coupon, comprising:
   (i) a reservoir tank defining a reservoir cavity for receiving a coupon;
   (ii) a fluid inlet means in fluid communication with said reservoir cavity;
   (iii) a fluid outlet means in fluid communication with said reservoir cavity;
   (iv) a coupon suspension member adapted for supporting a coupon within said reservoir cavity; and
   (v) a weight sensor coupled to said coupon suspension member;
wherein a fluid sample is capable of contacting a coupon supported by said coupon suspension member.

11. The apparatus of claim 10, wherein said apparatus further comprises a coupon supported by said coupon suspension member.

12. The device of claim 11, wherein said coupon is a substantially elongate planar member.

13. The apparatus of claim 10, wherein said reservoir tank further comprises a valve for draining a fluid sample from said reservoir cavity.

14. The apparatus of claim 10, further comprising a computer system which is associated with said weight sensor, said computer system being capable of computing data received from said weight sensor so as to determine the weight of a coupon and any biofilm deposition thereon.

15. The apparatus of claim 10, further comprising a first fluid circuit line in fluid communication with said reservoir tank, wherein said first fluid circuit line permits a fluid sample to enter said reservoir tank.

16. The apparatus of claim 10, further comprising a second fluid circuit line in fluid communication with said reservoir tank, wherein said second fluid circuit line permits a fluid sample to exit said reservoir tank.

17. The apparatus of claim 10, further comprising a pump for drawing a fluid sample from a fluid source to said reservoir tank.

* * * * *